(12) United States Patent
Goel

(10) Patent No.: US 8,754,205 B2
(45) Date of Patent: *Jun. 17, 2014

(54) EXTRACT OBTAINED BY A COMMERCIALLY VIABLE PROCESS FOR THE EXTRACTION OF FUROSTANOLIC SAPONINS FROM FENUGREEK SEEDS, IN WHICH ONE OF THE COMPOUNDS IN THE EXTRACT IS PROTODIOSCIN

(76) Inventor: Pawan Kumar Goel, Panchkula (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/474,594

(22) Filed: May 17, 2012

(65) Prior Publication Data
US 2012/0295857 A1 Nov. 22, 2012

Related U.S. Application Data

(62) Division of application No. 12/665,279, filed as application No. PCT/IN2008/000559 on Sep. 3, 2008, now Pat. No. 8,217,165.

(30) Foreign Application Priority Data

Jun. 17, 2008 (IN) .......................... 1439/DEL/2008

(51) Int. Cl.
*C07H 1/06* (2006.01)
*C07H 1/08* (2006.01)

(52) U.S. Cl.
USPC .......................................................... 536/128

(58) Field of Classification Search
None
See application file for complete search history.

(56) References Cited

U.S. PATENT DOCUMENTS

2007/0010462 A1 * 1/2007 Chibber ......................... 514/26

FOREIGN PATENT DOCUMENTS

WO    WO 2005060977 A1 * 7/2005

OTHER PUBLICATIONS

LookChem, Protodioscin product page, downloaded from the internet Apr. 8, 2013.*

* cited by examiner

*Primary Examiner* — Layla Bland
(74) *Attorney, Agent, or Firm* — Jackson Patent Law Office

(57) ABSTRACT

Disclosed is an extract obtained by a commercially viable process for the extraction of furostanolic saponins from fenugreek seeds, in which one of the compounds in the extract is protodioscin. The process includes providing plurality of fenugreek seeds and crushing the same by milling and grinding; performing a primary extraction on the prepared fenugreek seeds using a first hydrophilic polar solvent which is a lower primary aliphatic alcohol followed by ion-exchange chromatography; performing a secondary extraction after ion-exchange chromatography using a composite solvent; and decolorizing the final extract by use of activated charcoal concentration of the extract by heating and vacuum drying sieving the final powdered product.

2 Claims, 4 Drawing Sheets

Figure 1:
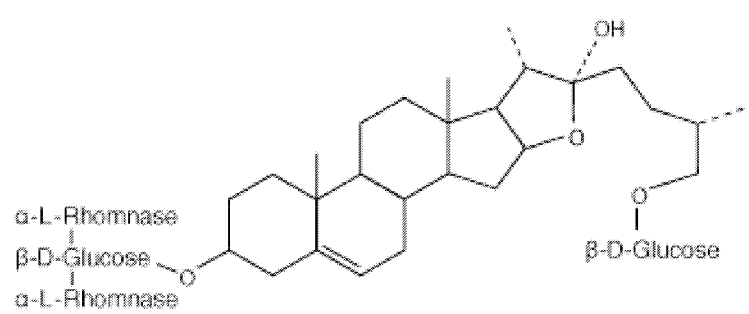

Fig. 1 Structure of Protodioscin

Figure 2:
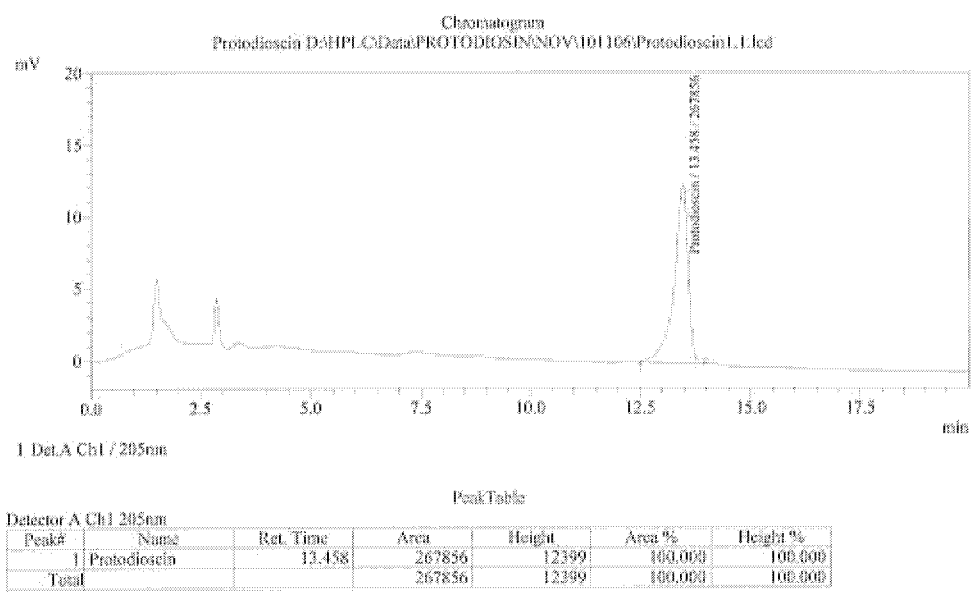

Fig. 2 : Chromatogram of reference standard of Protodioscin
(FUROSTANOLIC SAPONINS)

Figure 3:
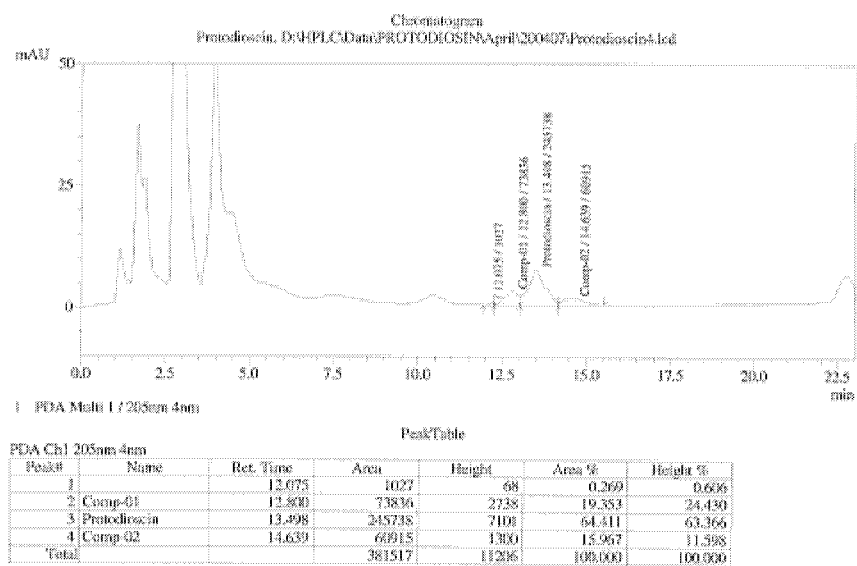

Fig. 3 : Chromatogram of extracts from Fenugreek seeds

Parameters: capillary 3189 V, sample cone 29 V, source temperature 120°C, desolvation temperature 250°C, gas flow 31 L/hr, and dissolution 550 L/hr

| Peak 1 | 13.75 | |
| Peak 2 | 13.90 | |
| Peak 3 | 14.22 | Trigoneoside IVa |
| Peak 4 | 14.42 | Glycoside F |
| Peak 5 | 14.85 | Protodioscin |

FUROSTANOLIC SAPONINS OF RICH EXTRACTS OF FINAL PRODUCT

EXTRACT OBTAINED BY A COMMERCIALLY VIABLE PROCESS FOR THE EXTRACTION OF FUROSTANOLIC SAPONINS FROM FENUGREEK SEEDS, IN WHICH ONE OF THE COMPOUNDS IN THE EXTRACT IS PROTODIOSCIN

CROSS-REFERENCE TO RELATED APPLICATION

This Application is a Divisional of U.S. National Phase 12/665,279, filed on Dec. 17, 2009, now U.S. Pat. No. 8,217,165 of International Patent Application PCT/IN2008/000559 of Pawan Kumar GOEL filed 3 Sep. 2008, for A NOVEL PROCESS FOR THE EXTRACTION OF FUROSTANOLIC SAPONINS FROM FENUGREEK SEEDS, the contents of which are herein incorporated by reference.

FIELD OF THE INVENTION

The field of invention pertains to chemistry. More specifically it pertains to a novel, commercially viable process for the extraction of bioactive, high-purity (>70%) furostanolic saponins from natural plant material i.e. fenugreek seeds.

BACKGROUND OF THE INVENTION

The present invention discloses a novel, commercially viable process for extraction of bioactive, high-purity (>70%) furostanolic saponins, particularly protodioscin (>30%) from fenugreek seeds. Protodioscin has Molecular Formula $C_{51}H_{84}O_{22}$, CAS No. 55056-80-9 and structure as given in FIG. 1.

Plants produce a vast and diverse assortment of organic compounds, the great majority of which do not appear to participate directly in their growth and development. These substances, traditionally referred to as secondary metabolites or plant natural products, often are distributed among limited taxonomic groups within the plant kingdom. The functions of secondary metabolites remain largely unknown, although a number of compounds have been associated with attributes useful to the plants e.g. protection against herbivores and protection against microbial infection, as attractants for pollinators and seed-dispersing animals, and as compounds that influence competition among plant species (allelochemicals). There is a growing interest in plant natural products, since these products often have a wide range of applications in different kinds of industries, including pharmaceutical industries, cosmetic industries, food industries, detergent industries, etc.

Secondary Metabolites of Commercial Interest—Saponins

Saponins are an example of a group of plant secondary metabolites. Saponins are glycosylated compounds classified as either triterpenoids, steroids, or steroidal glycoalkaloids. Saponins consist of one or two sugar moieties which are coupled to the aglycon (mono- and bisdesmosides, respecitvely). Saponins can be hydrolysed to sapogenins and sugar moieties by acid hydrolysis or enzymatic methods. Saponins are water soluble high molecular weight compounds with molecular weights ranging from 600 to more than 2,000 daltons.

Definition: In simple terms, saponins can be defined as "molecular complexes consisting of any aglycone (sapogenin) attached to one or more sugar chains."

Saponins thus describes a class of natural products which are structurally constructed of aglycone (triterpene or steroidal) and sugars (pentose(s), hexose(s), and/or uronic acid(s).

Accordingly, Saponins can be classified according to their aglycone composition as follows:
1) Triterpene glycosides
2) Steroid glycosides
3) Steroid alkaloid glycosides The Furostanolic saponins of the present invention fall in categories 2 and 3. The asymmetric distribution of their hydrophobic (aglycone) and hydrophilic (sugar) moieties confers an amphipathic character to these compounds which are largely responsible for their detergent-like properties. In some cases saponins may be acylated with organic acids such as acetic, malonic, angelic and others as part of their structure (Hostettmann K. and Marston A. Saponins, Cambridge University Press, Combridge. 1995.; Rouhi A M., Chem. Eng. News 73(37):28-35, 1995.; Leung A Y., and Foster S., Encyclopedia of Common Natural Ingredients Used in Food, Drugs, and Cosmetics, 2.sup.nd ed., John Wiley and Sons (Wiley-Interscience), New York (1996).

Saponins—Applications and Commercial Importance

Saponins have significant commercial uses. Until recently, saponins have been largely overlooked except in cases where their presence was considered toxic. There are human benefits to the use of galactomannans as well. In particular, it has been reported that fenugreek galactomannan is most evident in the lowering of cholesterol in both liver and blood plasma.

Cosmetic and detergent industries: Saponins have the ability of lowering surface tension and the word "saponin" also reflects this as "sapo" is the latin word for soap. Saponins therefore have potential applications in the cosmetic and in the detergent industries.

Pharmaceutical and therapeutic applications: Saponins furthermore have the ability of forming insoluble complexes with cholesterol, which makes some of them suitable for use in the pharmaceutical industry as cholesterol lowering agents. Saponins also have other therapeutical effects. Saponins from chestnut do e.g. possess anti-inflammatory characteristics. Saponins, when injected into the blood stream, are furthermore highly toxic due to their haemolytic properties. Saponins are usually relatively harmless when ingested orally. Steroidal saponins are of great interest owing to their relationship with such compounds as the sex hormones, cortisone, diuretic steroids, vitamin D and cardiac glycosides. Also, saponins are associated with formation of immunostimulating complexes (ISCOMs) (Morein et al., (1995) Clinical Immunotherapeutics 3: 461-475) that are useful in vaccine strategies.

Food and nutraceuticals industry: Saponins have flavoring, sweetening, antioxidant, foaming, complexing, sequestration, anticarcinogenic and antimicrobial properties. They could be used as an antioxidant, emulsifier, surfactant, ingredient for nutraceutical in food, health food and nutraceuticals industry and as such represent another value-added fraction for recovery.

Limitations to Widespread Use of Saponins

Cost: At present however, a major obstacle in exploiting the wide range of potential applications of saponins is the fact that commercially available saponins are relatively expensive. Commercially available plant extracts containing saponins are extracts of *Saponaria officinalis*, Quillaia bark and stem, *Castanea sativa* seeds, and extracts of various *Yucca* species. Liquorice root, primula root, and senega root can also serve as raw material for saponin extracts.

Limited raw material sources: A problem in this field is that the available sources of saponin extracts are relatively few. And in some cases, e.g. Quillaia bark, the plants are often sparse and expensive because they cannot be cultivated in an efficient manner. Usually the saponins are present in relatively low concentrations. The commercially available saponin extracts are thus often expensive and/or sparse.

Complex structures, which limit chemical synthesis: It should also be noted that saponins are quite complicated compounds and it has not so far been profitable to develop methods for chemical synthesis of these compounds.

Plant extracts containing saponins and sapogenins are thus of general interest within a wide range of different industries. There is therefore a growing need in the art for alternative sources of saponin extracts and these plant sources should preferably be cheap, easy to obtain, and preferably the saponin content should be relatively high. For the general description of saponins, extraction, production, and use of saponins reference is made to Ullman's Encyclopedia of Industrial Chemistry (1993), Vol. A23, pp. 485-498. Furthermore, the literature is abundant concerning the extraction, composition and specific effects of the individual saponins derived from plant materials.

Extraction of Saponins

Processes for extraction of commercially useful saponins and also bioactive saponins useful for pharmaceutical applications, from various plant sources have been described in prior art patents. However, saponins of prior art are quite different from the saponins of the present invention which are specifically 'furostanolic saponins'. None of the processes in prior art disclose a method for obtaining high-purity (>70%), bioactive fractions rich in furostanolic saponins particularly protodioscin (>30%) as has been disclosed in the present invention. The process is quite efficient and economical, resulting in yield of 2-4% of the purified bioactive fractions.

Processes for extraction of saponins as described in the prior art, from the major source, soybeans and other plant sources are discussed below. This is followed by discussion on processes for extraction of saponins specifically from sources which are regarded as rich sources of furostanolic saponins viz *Tribulus terrestris, Dioscorea deltoidea* and Fenugreek seeds. The present invention discloses a novel method for the extraction of high-purity (>70%) bioactive fractions rich in furostanolic saponins, particularly protodioscin from fenugreek seeds.

Extraction of Saponins from Soybeans: Processes for extraction of saponins from soybeans have been described in US patent applications no 20040013791, 20040101579, 20050123662 and 20050037099. These processes are quite different from the novel process of the present invention which is for extraction of a particular class of saponins i.e. furostanolic saponins, particularly protodioscin from fenugreek seeds, at high levels of >70% in the extracts. Moreover, quite a few processes utilize strong acidic or alkaline conditions for separation of the desirable saponins, whereas process of the present invention is a completely eco-friendly process, not utilizing any strong acids or alkalis. The entire process is carried out at or near neutral pH i.e. between pH 6 to 8.

It is known that soya contains saponin and isoflavone components in addition to saccharide and amino acid components, as well as proteins and mineral salts in amounts which depend on their geographical origin and the conditions under which the plant was cultivated and harvested. Soybean saponins are a generic name of saponins contained in starting soybeans and are present in concentrations of about 2 to 4% by weight. Saponins are classified into group A saponin, i.e., bisdesmoside saponin, wherein an aglycone skeleton is "soyasapogenol A" and sugar chains are attached to C-3 position and C-22 position of the aglycone through ether bonds; group B saponin, i.e., monodesmoside saponin, wherein an aglycone skeleton is "soyasapogenol B" and a sugar chain is attached to C-3 position of the aglycone through ether bond; and the like. In addition, saponin E, wherein a moiety of a sugar chain is acetylated is also reported (Kitagawa et al, Chem. Phrm. Bull, 33, (1985). Thus, saponin contents have been divided into three classes depending on the chemical structure of their triterpene components: soya saponins of groups A, B and E (Okubo K. et al., ACS Symp., Ser. 546, 330, 1994). 1 1 $R_1$ $R_2$ $R_3$ Group A; Saccharide Saccharide OH chain chain Group B Saccharide OH H chain Group E Saccharide —OH chain.

Isoflavone components consist of glucoside isoflavones (daidzin, genistin and glycitin) which can contain acyl radicals, e.g. malonyl radicals, linked to the saccharide chain. 2 2 $R_1$ $R_2$ $R_3$ Daidzin H H D-Glucose Glycitin $OCH_3$ H D-Glucose Genistin H OH D-Glucose Daizdein H H H Glycitein $OCH_3$ H H Genestein H OH H US patent application no 20040013791 discloses a soy protein material having a very low isoflavones content and a high content of saponins. The process for producing the low isoflavones, high saponins soy protein material involves removing fiber from a defatted soybean material and obtaining a liquor that is subsequently pasteurized. Next, sugars and other small molecular weight components are optionally removed from the liquor using membrane separation to increase the protein content of the final material. The resulting liquor or retentate is subjected to adsorptive removal of isoflavones, and is optionally pasteurized and spray dried. The process thus involves pasteurization and membrane filtration steps, which are not used in the process of present invention at all. Also, there is no disclosure about any process for obtaining high-purity (>70%) bioactive fractions rich in furostanolic saponins, particularly protodioscin as has been disclosed in the present invention.

US patent application no 20040101579 relates to novel extracts obtained by extraction of ripe complete soya beans or from oil-free soya flour (*Glycine max* (L.) MERRIL, Leguminosae family), their production and formulations containing these extracts. The novel extracts are characterized by their content of isoflavones and saponins in defined ratios. The extracts are characterized by a content of glucoside isoflavones of at least 13% by weight and a content of 0.6 to 1.5 parts by weight of group 3 soya saponins and per 1 part by weight of glucoside isoflavones. The extract is mainly for treating pre- or post-menopausal symptoms in a female subject and also breast cancer in females. The application does not describe any process for obtaining fractions rich in furostanolic saponins (>70%), particularly protodioscin as has been disclosed in the present invention. Also, the present invention discloses furostanolic saponin rich fractions, particularly protodioscin, to enhance testosterone production and not for treatment of menopausal symptoms or cancer.

United States Patent Application no. 20050123662 describes a simple and novel process for obtaining highly pure saponins at a high yield, on an industrial scale from soybeans, starting from isoflavones extracted from soybeans. The same is discussed in detail as follows:

Conventionally, in order to obtain a material containing saponins at a high concentration from starting soybeans such as whole soybeans, defatted soybeans, soybean hypocotyls, and the like, it was known that appropriate separation of saponins from isoflavones is important. A general scheme in the conventional process consisted of first stage production steps involving extraction with a solvent such as a lower alcohol or acetone; adsorption of the resultant extract with a synthetic adsorption resin such as HP-20 and XAD-2 or activated carbon; washing the absorbed extract with a low concentration of a lower alcohol (10 to 40% by volume) and purification by gel filtration such as LH-20, or the like, or partition chromatography after carrying out and then elution of a fraction containing saponins with a high concentration of a lower alcohol (70 to 80% by volume).

However, in order to obtain a highly pure saponin fraction in the above-described processes, the final purifying step by means of gel filtration or partition chromatography was required and led to a low yield of saponins to about 1 to 2%. This was problematic from the viewpoints of facility costs and production efficiency for industrially putting such a process into practice. On the other hand, in order to extract saponins with a solvent at a high yield, the extraction was conventionally being carried out at a high temperature. However, even when such extraction was carried out, material containing saponins which satisfied requirements of high purity and high yield without complicated operation, could not be obtained.

To enhance the yield of saponins, raising temperature during extraction or altering pH are well known conventional approaches which were utilized by the inventors. However, it was found that though yield of saponins could be improved under high temperature conditions, but at the same time solid materials other than saponins also got extracted, which conversely caused a decrease in purity of saponins. For purification, two complicated stages further were required, which though resulting in pure saponin fractions, resulted in poor yields.

The inventors observed that hydrophobicities of saponins are particularly close to those of isoflavone glycoside, acetyl isoflavone glycoside, and isoflavone aglycone, among isoflavones. Therefore, it is difficult to separate them by utilizing these properties. Among isoflavones, malonyl isoflavone glycoside has a dissociation group and thus has a relatively high polarity. Therefore, malonyl isoflavone glycoside can be easily separated from saponins with an adsorbent. In a natural state, soybeans contain a largest amount of malonyl isoflavone glycoside. However, malonyl isoflavone glycoside is unstable to heat and is easily converted into isoflavone glycoside, acetyl isoflavone glycoside, or isoflavone aglycone by heating, which is typically employed in conventional processes. Once these compounds were generated as a result of heating, it became very difficult to separate these from saponins Hence, if heating could be avoided an multistage extractions carried out, relatively pure saponin fractions at high yields could be obtained. The same was tried and found to be successful by the inventors of the above prior art application. When multi-stage extraction was carried out under mild conditions at which conversion of malonyl isoflavone glycoside in starting soybeans into isoflavone glycoside, acetyl isoflavone glycoside, or isoflavone aglycone was avoided, it was found that saponins could be separated from isoflavones extremely efficiently only by subsequent one-stage purification step, i.e., treatment with an adsorbent to obtain highly pure saponins at a high yield. Thus, a simple and easy process for producing a saponin-containing material having an extremely high purity at a high yield on an industrial scale was standardized.

A comparison of the steps involved in the process of the above prior art document and the process as described in the present invention shows that the processes are entirely different, though both are aimed at extraction of saponins. The process of the prior art document consists of one stage purification whereas process of the present invention is a multi-step purification. Secondly, process of the prior art is directed towards saponin extraction from soybeans, whereas process of the present invention is directed toward the extraction of specifically furostanolic saponins rich in protodioscin from fenugreek seeds. As the nature and content of the contaminating compounds i.e. isoflvanones and also nature of the saponins itself is different in both cases, the extraction processes in both cases are different.

Moreover, the saponins extracts of the prior art document as discussed above, are intended for a variety of physiological activities such as anti-obesity activity, antioxidant activity, and an immunity activation activity. Then, when a material containing saponins at a high concentration is available, the material can be utilized by simply adding it to various foods and drinks. In contrast, the saponins of the present invention are specifically furostanolic saponins, particularly protodioscin intended for elevating testosterone levels and promoting anabolism and to be consumed in well-defined dosage forms e.g. tablets or capsules.

United States Patent Application no. 20050037099 describes a simple and inexpensive semi-industrial technology for isolation and purification of active plant compounds, including isoflavones, sitosterols, saponins (sapogenins), and phospholipids for topical application. Soybeans are particularly suitable as a plant source; however, any other isoflavone-containing plants (e.g., red clover and kudzu) can be used as a source of active compounds, in the process of the described invention. Molasses, enriched fluor or any other non-protein concentrate can be used as a source material for the isolation and purification process. The composition of the above invention is suitable for topical application for preventing and treating changes associated with skin aging and formation of abnormal skin lesions. The composition is derived by hydrolyzing a source composition in an acidic solution. The source composition can be, e.g., a soy composition and can include one or more isoflavones, phytoestrogens, sitosterols and saponins. After hydrolysis, water is added to the acidic solution to produce a first precipitate, which is then dissolved in an alcohol solution. The alcohol solution is then separated from undissolved portions of the first precipitate, and the alcohol in the separated alcohol solution is eliminated to produce a second precipitate of solids that were dissolved in the alcohol. This second precipitate is then dissolved in an organic solvent to produce a composition suitable for inclusion in a dermatological or cosmetic preparation.

Thus, the composition described is a mixture of various phytocompounds and the extraction process is also not specific for saponins alone. Moreover, it involves use of acids to produce a first precipitate and does not involve any chromatographic purification steps. In contrast, the present invention is specifically directed towards an extraction process for obtaining high-purity (>70%) fractions rich in furostanolic saponins, particularly protodioscin, from fenugreek seeds. It does not involve use of any strong acids at all. All steps are carried out at primarily neutral pH i.e. 6 to 8. Also, the purification process of the present invention is a multi-step process involving chromatographic purification also.

Extraction of Saponins from Other Plant Sources:
   1. *Anemone Raddeana*
   2. Edible beans,
   3. Plants of the family Myrsinaceae,
   4. *Quillaja saponaria* Molina (soap tree)
   5. *Sapindus trifoliatus*
   6. Wenguanguo or *Xanthoceras sorbifolia*
   7. Plants from the genus Panax (*Panax ginseng, Panax quinquefolium* and *Panax notoginseng*)
   8. Honeysuckle (*Lonicera japonica* Thunb.)
   9. Plant species, notably from the genera *Smilax, Asparagus, Anemarrhena, Yucca* and *Agave*
   10. *Xanthoceras sorbifolia*
   11. Butter tree of the Sapotaceae family
   1. *Anemone Raddeana:* US patent application no 20040067263 discloses a process for preparation of a crude saponin rich extract from rhizome, stem, leaf, flower, and fruit of *Anemone Raddeana*. The same is useful for treating malignant neoplasm diseases. The bioactive saponins disclosed are thus quite different from that of the present invention, which specifically relates to extraction of high purity (>70%), bioactive furostanolic saponins, which enhance testosterone production.

2. Edible beans: United States Patent Application no. 20040131749 relates to a composition comprising a phytochemical, in particular, polyphenolic extract derived from edible beans and containing one or more of the following: anthocyanins, flavonols, proanthocyanindins, isoflavones, lectins, saponins, sapogenins, vitamins, minerals and functional proteins. The invention further provides a process for the production of an anthocyanin or flavonol extract from an edible bean source, the process comprising providing the edible beans, contacting the edible beans with an aqueous solution to produce an aqueous extract, and separating the aqueous extract from the edible beans. The present invention relates, in general, to a process of isolating phytochemical, in particular polyphenolic compounds from commercial edible bean processing waste streams for use as natural colors and functional foods and extracts obtained by such process. These compounds also have potential for use as nutraceutical ingredients in the following health related areas: antioxidants, cardiovascular disease protection, anti-diabetic effects, anti-inflammatory effects, antiviral properties, anti-tumorgenic properties, improvement of night vision, anti-inflammatory activity and anti-stress. The resulting extracts can be formulated for treatment of these conditions. Further utilization can occur for use as cosmetic ingredients and natural colors. The invention also relates to novel compositions comprising extracts prepared by the process of the invention. Though saponins are present as components in the polyphenolic extracts of this invention, they are neither the main ingredients nor of the same nature or biological action as the saponins of the present invention, which are specifically bioactive, high-purity (>70%), furostanolic saponins, particularly protodioscin. Moreover, the intended biological use of the bioactive saponins in both is entirely different—the former proposing use of the polyphenol extracts, containing saponins for a wide variety of physiological processes while the present invention specifically pertains to furostanolic saponins, particularly protodioscin, for enhancing testosterone levels and anabolic processes.

3. Plants of the family Myrsinaceae: United States Patent Application no. 20040138151 discloses antiprotozoal saponins isolated from plants of the family Myrsinaceae and used to decrease the infectiousness of and reduce the mortality associated with protozoan parasites of the genus *Leishmania* which are responsible for a group of conditions known as leishmaniases. The invention relates to one or more triterpene saponins obtainable by the processes described for extraction of the compounds, whether as a mixture or as isolated products. The saponins described i.e. triterpene saponins and their methods of extraction are quite different from the present invention which refers specifically to extraction of only one specific category of saponins ie. high-purity (>70%) furostanolic saponins, particularly protodioscin, from fenugreek seeds.

4. *Quillaja saponaria* Molina (soap tree): United States Patent Application no. 20050175623 discloses compositions comprising saponins, extracted from *Quillaja saponaria* Molina (soap tree), which are used as therapeutic compounds for the treatment and prevention of cancer diseases or as a dietary supplement that offers tumor cell killing and tumor cell inhibition, and also as a anticancer potentiator with other anticancer agents. The saponin derived novel anticancer agents, include both triterpenoid and steroidal saponins found in the bark of *Quillaja saponaria* Molina (soap tree). The Saponins include but are not limited to, sapogenins, and its prosapogenins with one or more sugar moieties. The method of extraction of saponins has not been disclosed as the same were purchased from commercial sources as 'ready-to-use' extracts. Invention is thus directed towards novel uses of saponin extracts, rather than disclosing a process of extraction of furostanolic saponins as has been described in the present invention.

5. *Sapindus trifoliatus:* United States Patent Application no. 20050249831 discloses a process for a herbal extract comprising a mixture of saponins obtained from *sapindus trifoliatus* (Common name, Ritha) for anticonvulsant activity. The pericarp of the fruit of the plant, which constitutes 62% of the fruit contains, glucose, saponins and primary metabolites. The saponins present in the fruit on acidic hydrolysis give the triterpenoid hederagenin, D-glucose, L-rhamnose and D-xylose and Arabinose. [The Wealth of India, Vol IX, CSIR Publication, by NISCOM, New Delhi, India, 1998, pp 227-29]. The extract is prepared from the pericarp of the fruit of *S. trifoliatus*, and compres from 4 to 8% w/w of hederagenin as the bioactive component and ii. pharmaceutically acceptable additives. The process comprises the steps of extraction of the pericarp of the fruit of *S. trifoliatus* with water or an alcohol or a mixture thereof at ambient to boiling temperature for 0.5 to 24 hours, b. lyophilization of the aqueous, alcoholic or aqueous alcoholic extract containing a mixture of saponins to give a lyophilized powder, containing a mixture of saponins, and c. reconstitution of the lyophilized extract in water to achieve a concentration of hederagenin between 0.001 to 1.0 (% w/v). The invention discloses the preparation of bioactive pure compounds from a mixture of triterpenoid saponins extracted from the pericarp of *S. trifoliatus*.

However, the present invention is directed specifically towards the extraction of furostanolic saponins, which are a separate category of saponins from the triterpenoid saponins as detailed in the above patent. The extraction process of the present invention is altogether different and results in furostanolic saponin rich fractions (>70%) and not extraction of any triterpenoid saponins.

6. Wenguanguo or *Xanthoceras sorbifolia:* United States Patent Application no. 20050276872 discloses the extraction of saponins and other constituents including alkaloids, coumarins, saccharides, proteins, polysaccharides, glycosides, tannins, acid, flavonoids and others from husks or fruit-stems or seed shells or leaves or branches or stems or kernels or roots or barks of Wenguanguo or *Xanthoceras sorbifolia*. The category of saponins is oleanene triterpenoidal saponin with the characteristics that at least one angeloyl group is attached to Carbon 21 or/and 22, or/and linked to the sugar. The compounds of the present invention have various pharmaceutical and therapeutic applications. In contrast, the saponins of the present invention are not triterpenoid saponins, but high-purity (>70%) steroid saponins (furostanolic saponins) extracted from fenugreek seeds.

7. Plants from the genus *Panax* (*Panax ginseng, Panax quinquefolium* and *Panax notoginseng*): United States Patent Application 20060013897 discloses compositions for cancer therapy comprising two or more saponins and/or sapogenins. Ginseng has long been recognized as a general tonic and a benign and safe herb. Many of the components of ginseng have been isolated and have been classified as: ginsenosides, carbohydrates, nitrogenous compounds, fat-soluble compounds, vitamins and minerals. The saponins derived from ginseng (also called "ginsenosides") are believed to be the main active components of ginseng. Saponins, in general, are composed of a sugar portion (glycon) and a non-sugar portion (aglycon or sapogenin). The sapogenins in ginseng, the backbone of saponins, are further classified into three types: protopanaxadiol and protopanaxatriol (which are tetracyclic terpenoids of the dammarane series), and oleanoic acid. More than dammarane-type saponins have been isolated from *Panax ginseng* C. A. Meyer, which vary in the number and type of monosaccharide residues present in the sugar side chains. The individual ginsenosides are named Rx according to their mobility on thin-layer chromatography plates. Examples of known ginsenosides include those in groups Ra through Rh. The isolation of three new dammarane-type saponins (named Rk1 to Rk3) from heat-processed ginseng has also been reported recently (see Park, I. H. (2002) Arch Pharm Res. 25: 428-32). No specific extraction process for extraction of the saponins has been disclosed, as emphasis is on use of the compounds for cancer treatment and not the extraction process. It has been indicated in the patent application that extracts can be prepared from plant material by standard techniques known in the art. The inventors cite a variety of strategies available for preparing extracts from plant material, the choice of which depends on the ability of the method to extract the components required for the compositions of the present invention. Examples of suitable methods for preparing extracts include, but are not limited to, hydro-distillation, direct steam distillation, solvent extraction, and Microwave Assisted Process. The steam and components can then be condensed and the extract collected. Organic solvents can also be used to extract the active components. Non-limiting examples of such organic solvents include methanol, ethanol, hexane, and methylene chloride. As an alternative to aqueous or organic solvents, microwaves can be used to excite water molecules in the plant tissue which causes cells to rupture and release the compounds trapped in the extracellular tissues of the plant material. To confirm the presence of the desired components in the extract (i.e. the saponins and/or sapogenins), a variety of analytical techniques well known to those of skill in the art may be employed. Such techniques include, for example, chromatographic separation of organic molecules (e.g., gas chromatography or liquid chromatography), mass spectroscopy, or other spectroscopic techniques (such as infra-red, ultra-violet or nuclear magnetic resonance spectroscopy).

Thus, the above patent application does not disclose a specific extraction process for the saponins of bioactive interest but only refers to existing conventional methods in general. Moreover, the saponins are altogether different from the saponins of the present invention which is specifically for steroidal saponins i.e. furostanolic saponins, particularly protodioscin. Also, the extraction process of saponins in the present invention is not a generalized scheme but is a specific novel process for the preparation of furostanolic saponin rich, bioactive extracts of high purity (>70%) from fenugreek seeds and has been described in detail.

8. Honeysuckle (*Lonicera japonica* Thunb.): United States Patent Application no. 20060014240 discloses an extraction and purification method of active constituents including sweroside from for honeysuckle stem (stem of honeysuckle where leaves are removed) by removing tannins, hardly soluble flavonoids, saponins, and the like. Thus obtained active constituents have better anti-inflammatory and analgesic effect, are safer and more stable than the conventional active constituents obtained from honeysuckle flower or honeysuckle leaves, and include sweroside which is an effective active ingredient of anti-inflammatory and analgesic drug. It discloses only the removal of saponins as a step for purification of the compounds of interest and does not disclose any specific process for purification of saponins at all.

9. Plant species, notably from the genera *Smilax, Asparagus, Anemarrhena, Yucca* and *Agave:* United States Patent Application no. 20060182817 discloses the use of a number of saponins and sapogenins, notably those of steroidal structure, in the treatment of cognitive disfunction and similar conditions. The saponins and sapogenins of principal interest in certain aspects of the present invention occur naturally in a range of plant species, notably from the genera *Smilax, Asparagus, Anemarrhena, Yucca* and *Agave*. The species presently of greatest interest include Smilax regelii Kilip & Morton—commonly known as *Honduran sarsaparilla; Smilax aristolochiaefolia* Miller—commonly known as Mexican sarsaparilla; *Smilax omata* Hooker—commonly known as Jamaican sarsaparilla; *Smilax aspera*—commonly known as Spanish sarsaparilla; *Smilax glabra* Roxburgh; *Smilax febrifuga*—Kunth—commonly known as Ecuadorian or Peruvian sarsaparilla; *Anemarrhena asphodeloides* Bunge; *Yucca schidigera* Roezl ex Ortgies; and *Yucca brevifolia* Engelm. Saponins and sapogenins which may be of interest also occur naturally in other genera, for example *Dioscorea, Trillium, Solanum, Strophanthus, Digitalis* and *Trigonella*. As indicated above, some saponins and sapogenins from these sources possess undesirable properties and are thus not recommended for use in the invention. Methods of treatment, and pharmaceutical compositions based on specific saponins/sapogenins are also disclosed. However, there is no disclosure at all about the extraction process for the saponins of interest.

10. *Xanthoceras sorbifolia:* United States Patent Application no. 20050220910 discloses compositions, methods and process of producing extracts from *Xanthoceras sorbifolia*. The extract comprises alkaloids, coumarins, saccharides, proteins, polysaccharides, glycosides, saponins, tannins, acid, flavonoids and others. The composition can be used for treating cancer, arthritis, rheumatism, poor circulation, arteriosclerosis and a wide variety of other ailments. The invention provides compounds comprising at least one sugar, a triterpene, such as Sapogenin, and at least one side chains at Carbon 21 and 22, such as Angeloyl groups. The structure of the compound has been described and has formula of $C_{57}H_{88}O_{23}$ and the name 3-O-[.beta.-D-galactopyranosyl (1.fwdarw.2)]-.alpha.-L-arabinofuranosyl(1.-fwdarw.3)-
.beta.-D-glucuronopyranosyl-21,22-O-diangeloyl-3.beta.,
15.alpha.-16.alpha.,21.beta.,22.alpha.,
28-hexahydroxyolean-12-ene, also known as Xanifolia-Y. This compound was isolated from *Xanthoceras sorbifolia*.

The extraction process of the bioactive saponin has not been disclosed. Also, the bioactive saponin as disclosed in the above patent application (Molecular formula $C_{57}H_{88}O_{23}$) is quite different from the bioactive saponin of the present invention, which is specifically a furostanolic saponin, protodioscin having molecular formula $C_{51}H_{84}O_{22}$.

11. Butter tree of the Sapotaceae family: United States Patent Application no. 20050233016 discloses a method for preparing a saponin-containing aqueous extract on the basis of a waste product from a butter tree of the Sapotaceae family, said method comprising the following steps: (i) mixing one part waste product with 4-30 parts of water; (ii) incubating the mixture formed in step (i) under alkaline conditions; and (iii) recovering an aqueous extract containing saponins by removing solids from the alkaline mixture formed in step (ii). The invention also relates to saponin-containing aqueous extracts obtainable by said method and uses thereof. Also, the saponins obtained are quite different from the saponins of the present invention. In the above patent, the extract obtained is composed of a diversity of water soluble types of constituents. One group is the tannins. The tannins are a group of simple and complex phenol, polyphenol and flavonoid compounds, bound with starches, and often they are just classified as tannins simply as they contain variations on gallic acid. One simple way of fractionating the constituents is by applying ultra filtration to separate the constituents according to their molecular size. Extracts obtained by the methods of the invention may be further subjected to a hydrolysing step converting a fraction of the saponins to their corresponding sapogenins. The sapogenin part may be further purified by recrystallisation and/or derivatised with fatty moieties to make it soluble in e.g. oil.

The extraction process as described in the above cited document is not restricted to a particular class of saponins, but is a very broad process encompassing a variety of water soluble compounds from waste by product of butter tree. Applications envisaged for the extracts include use as food additives, food ingredients, ingredients in detergent products; cosmetic product; in a pharmaceutical product for topical application; active component in a pharmaceutical product for lowering the level of serum cholesterol in a human being or in other mammals; as an active compound in a pharmaceutical product for treatment of inflammatory diseases; as an active compound in a pharmaceutical product for systemic administration, e.g. treatment of cardiac disorders or diuretic disorders, or vitamin D associated disorders; as an active component in the manufacture of a nutritional supplement; as an ingredient in immunostimulatory complexes (ISCOMs). Also, the plant extract e.g. may be used as a wetting agent or emulsifier. The extract can be used as a wetting agent in many applications e.g. spraying of pesticides and herbicides, dust control, etc. Furthermore it can be formulated with other surfactants, builders and ingredients normally used in detergents.

The process is quite different from the process of the present invention which is not based on aqueous extraction alone, but utilizes organic solvents and the process of gel filtration chromatography. Also, the saponins obtained are quite different from the saponins of the present invention. In the above patent, the extract obtained is composed of a diversity of water soluble types of constituents, whereas the process of the present invention discloses a specific method for extraction of furostanolic saponins as high purity fractions (>70%), from fenugreek seeds, only for pharmaceutical use and no other intended use.

Furostanolic Saponins

Furostanolic saponins (FUROSTANOLIC SAPONINS) are important phytochemicals. They are extracted from plants and are useful in the treatment of various diseases, as components of health foods and also as nutraceuticals. Furostanolic saponins have been shown in vertebrate studies to have positive effects on anabolic processes, testosterone production, appetite stimulation, and immune function. They are used for treating sexual impotency as well as for boosting muscle growth. Both of these effects stem from their ability to enhance testosterone levels in the body.

Current research indicates that the dominant furostanolic saponin, PROTODIOSCIN is the active ingredient responsible for testosterone-boosting effects. (CAS No. 55056-80-9; Molecular Formula $C_{51}H_{84}O_{22}$). This steroidal saponin appears to stimulate the release of luteinizing hormone (LH) from the pituitary gland. LH then travels via the bloodstream to the testicles, where it stimulates testosterone production. Protodioscin is also believed to increase dehydroepiandrosterone (DHEA) production by the adrenal glands. This steroid precursor becomes testosterone.

Extraction of Saponins from Sources which are Regarded as Rich Sources of Furostanolic Saponins Some of the commonly known plant sources regarded as rich sources of Furostanolic Saponins are *Tribulus terrestris, Dioscorea deltoidea, Avena sativa* and Fenugreek.

a) *Tribulus terrestris:* This herb is cultivated in many parts of the world, including the United States, Mexico and Asia. It it is used for treating sexual impotency, as well as for boosting muscle growth. Both of those effects stem from its ability to enhance testosterone levels in the body. Current research indicates that the dominant furostanolic saponin, protodioscin is the active ingredient in *Tribulus* extracts that affords it its testosterone-boosting effects.

b) *Dioscorea deltoidea* This climbing plant grown in Asia is used for numerous purposes-from treating asthma to killing lice. Its high concentration of furostanolic saponins makes it a good supplement for boosting testosterone levels in a manner similar to *Tribulus terrestris* and fenugreek.

c) *Avena sativa: Avena sativa* is the scientific name for oats. An extract from the plant has the ability to increase testosterone levels by enhancing LH release. Maybe that's why oatmeal is such a bodybuilding staple. A bowl of oatmeal probably doesn't have enough of the active compound avenacosides to give a noticeable boost, but concentrated *Avena sativa* extract does. Avenacosides are a type of plant saponin similar to furostanolic saponins.

d) *Trigonella foenum-graecum* (Fenugreek): The fenugreek herb is native to southern Europe, the Mediterranean region and western Asia. It has numerous health benefits, including increased libido, elevated testosterone and increased insulin release. As with *Tribulus terrestris*, this herb contains a high amount of furostanolic saponins (FUROSTANOLIC SAPONINS). Therefore, fenugreek extract works in a manner similar to *Tribulus*-elevating testosterone via increases in the amount of LH and DHEA the body produces. Some bodybuilders report having a better appetite when taking fenugreek extract-a great benefit for hardgainers.

Extraction of Sponins from *Tribulus*

United States Patent Application no. 20050163874 discloses a process for obtaining a pharmacological substance characterized by that it is a combination of bio-active trivalent chromium and a complex of steroid saponins obtained from the leaves, stems and fruit of the plant *Tribulus Terrestris* L. and consisting of furostanols, spirostanols, sapogenins, sterols, flavonoids and other biologically active substances typical of this plant. The pharmacological substance based on biologically active substances obtained from the plant *Tribulus Terrestris* L., characterized by processing an extract from the plant *Tribulus Terrestris* L. at negative temperatures until obtaining a complex of steroid saponins. Neither the extraction temperatures nor details of the solvents and conditions for extraction have been disclosed, though composition has been described in detail.

The complex contains furostanols, spirostanols, sapogenins, sterols, flavonoids and other biologically active substances typical of this plant in the following ratios in % by weight: Furostanols from 1 to 35%, Spirostanols from 1 to 40%, sapogenins, from 0.01 to 30% sterols from 0.01% to 15%, and flavonoids and other bio-active substances, from 0.0001 to 15%. The same is indicated to be used as an agent reducing blood sugar, improving blood circulation and especially blood circulation in veins and capillaries of the limbs of diabetic patients, reducing bad cholesterol level, increasing good cholesterol concentration, maintaining cardiovascular and liver functioning with an additional prophylactic or healing effect on the immune system and the immune resistance.

In contrast, the process of the present invention does not utilize extraction at negative temperatures nor does it involve addition of any metal such as chromium to the extracts. Moreover, the extraction process of the present invention is not directed towards extracting a mixture of various saponins as is given in the above patent of the prior art. Rather, it is directed only towards extracting one specific class of saponins viz. furostanolic saponins particularly protodioscin, present at a high purity level of >70% from seeds of fenugreek. No other parts of the plant are used. Also, the bioactive function of the saponins of the present invention is entirely different from that in the prior art document viz. elevation of testosterone levels, which is not mentioned at all in the prior art document.

United States Patent Application no. 20050208158 relates to a pharmacological composition based on biologically active substances obtained from leaves, stems and fruit of the plant *Tribulus terrestris* L. to be used as an agent strengthening the immune system, increasing T-cells and anti-bodies number and testosterone quantity in human organism and having a strong anti-virus and anti-inflammatory effect in the form of a medicine or as an addition to food.

The pharmacological composition represents a combination of bio-active zinc, bio-active selenium and a complex of steroid saponins obtained from leaves, stems and fruit of the plant *Tribulus terrestris* l. and consisting of furostanols spirostanols, sapogenins, sterols, flavonoids and other biologically active substances typical of this plant. The pharmacological substance based on biologically active substances obtained from the plant *Tribulus Terrestris* L., characterized by processing an extract from the plant *Tribulus Terrestris* L. at negative temperatures until obtaining a complex of steroid saponins. The complex of steroid saponins contains furostanols, spirostanols sapogenins, sterols, flavonoids and other biologically active substances typical of this plant in the following ratios in % by weight: furostanols from 1 to 90%, spirostanols from 1 to 75%, sapogenins, from 0.01 to 80%, sterols from 0.01% to 23%, flavonoids and other bio-active substances from 0.0001 to 24%. Pharmacological composition according to the invention is characterized in that the complex of steroid saponins obtained from the leaves, stems and fruit of the plant *Tribulus Terrestris* L., bio-active zinc and bio-active selenium are all included in a pharmaceutical or nutritive base in the following ratios in % weight: a complex of steroid saponins obtained from *Tribulus Terrestris* L. from 1 to 40%, bio-active zinc from 0.001 to 2%, pharmaceutical or a nutritive base from 1 to 55%.

The composition is to be used as an agent for strengthening the immune system, increasing T-cells and anti-bodies number and testosterone quantity in human organism and having a strong anti-virus and anti-inflammatory effect in the form of a medicine or as an addition to food.

However, neither the extraction temperatures nor details of the solvents and conditions for extraction have been disclosed, though composition has been described in detail. In contrast, the process of the present invention does not utilize extraction at negative temperatures nor does it involve addition of any metals such as zinc or selenium to the extracts. Moreover, the extraction process of the present invention is not directed towards extracting a mixture of various saponins. Rather, it is directed only towards extracting one specific class of saponins viz. furostanolic saponins particularly protodioscin, present at a high purity level of >70% from seeds of fenugreek. No other parts of the plant are used.

Extraction of Saponins from *Dioscorea Deltoidea*

US patent application number 20070213280 describes a process for extraction of steroidal saponins (furostanolic saponins) from traditional Chinese medicine and natural products. Extraction procedures for two varieties of *Discorea* viz. *D. nipponica* and *D. futschauensis* have been described. The basic procedure in both is the same involving the steps of:
1. Extraction with alcohol by heating and refluxing
2. Suspending the extract in water to get a water soluble and water insoluble portion
3. Passing the extract through a resin column and eluting with water followed by increasing concentrations of ethanol viz. 10%, 50% and 95%.
4. Taking the 50% ethanol eluted fraction and subjecting it to silica gel column chromatography on column with granularity of 45.about.75 um, using a specific elution mixture of CH3Cl, CH3OH and H2O in the ratio of 8:2.5:0.1 and methanol, step by step
5. Vaporizing and concentrating the eluted solution under decreased pressure, incorporating the crystals of component fractions and re-crystallizing the crystals to get compounds of interest viz. MethylProtodioscin (MPD) and Pseudoprotodioscin (PPD).

Extraction of Saponins from Fenugreek (*Trigonella foenum-graecum*)

Fenugreek (*Trigonella foenum-graecum*) has attracted considerable interest as a natural source of soluble dietary fiber and diosgenin (sapogenins). The fenugreek seed contains a central hard, yellow embryo surrounded by a corneous and comparatively large layer of white, semi-transparent endosperm. This endosperm contains galactomannan gum. The endosperm is surrounded by a tenacious, dark brown husk. The color of the gum fraction depends upon the amount of outer husk (brown color) and cotyledon (yellow color) present. There are commercial uses for the various fractions of the fenugreek seed. The commercial fenugreek oleoresins are used as an ingredient for imitation maple flavors and is effective in butter, butterscotch, black walnut, nut and spice flavors. Another fraction of the fenugreek seed has been found to be a quantity of saponins.

Fenugreek seed saponins are steriodal in nature with diosgenin as the main sapogenin. Disogenin is used by the drug industry as a precursor to progesterone (steriod hormones) which is used in the manufacturing of oral contraceptives.

Processes for the extraction of bioactive fractions, not necessarily confined to saponins, from fenugreek seeds have also been described in the prior art. However, the bioactive fractions as described in the prior art are quite different from that of the present invention. None of the processes of the prior art reveals a process for the extraction of high-purity (>70%), bioactive furostanolic saponins fractions, particularly protodioscin, from fenugreek seeds.

Inventions of The Prior Art are Briefly Discussed Below:

U.S. Pat. No. 5,997,877 discloses a process for extraction of various useful fractions from fenugreek seeds (*Trigonelle foenum-graecum*). The process has a high yield rate, and provides a number of high-quality fractions of the fenugreek seed including a soluble dietary fiber fraction, de-flavored fenugreek seed, high-protein fenugreek meal, and dioscin and other saponins, along with the fenugreek oleoresins which have conventional commercial use. The main steroidal saponin extracted by the process of the invention is diosgenin, used by the drug industry as a precursor to progesterone (steriod hormones) which is used in the manufacturing of oral contraceptives. There is no disclosure about a processss, particularly for extraction of protodioscin rich furostanolic saponins, as has been disclosed in the present invention.

US patent application no. 20010024665 also discloses method for obtaining useful fraction i.e. substantially pure fixed oil(s), oleoresin and dietary fiber from Fenugreek seeds. The method employs two different solvent extraction stages, wherein the first extraction isolates fixed oils and the second extraction isolates oleoresin. The dietary fiber remaining after extraction is clean, approximately light yellow to light brown, substantially tasteless and substantially odorless.However, it does not disclose any process or method for extraction and purification of fursotanolic saponins as in the present invention.

US patent application no. 20040009247 discloses Fenugreek seed bio-active compositions for facilitating and supporting the metabolism and transport of glucose and carbohydrates into muscle cells and methods for extracting same. The bio-active compounds include 4-hydroxyisoleucine and one or more amino acids selected from the group consisting of arginine, aspartate, threonine, serine, glutamate, proline, glycine, alanine, cysteine, valine, methionine, isoleucine, leucine, tryptophan, phenylalanine, ornithine, lysine, histidine, gamma-amino butyrate, and trimethylhistidine. The composition of bio-active compounds includes between about 10% and 70% of 4-hydroxyisoleucine and between about 20% and 40% of the amino acids. Thus, the disclosure in the prior art is restricted to extraction of amino acid rich fractions only from fenugreek seeds. There is no disclosure at all regarding any extraction procedure for furostanolic saponins, particularly protodioscin rich fractions from fenugreek seeds as in the present invention.

United States Patent Application no. 20050153001 discloses a fenugreek seed extract to lower blood cholesterol. The extract is prepared fresh and involves merely boiling the soaked seeds of fenugreek in a cup of water for 5-7 minutes. There is no disclosure regarding the contents of the extract. In contrast, the extraction process of the present invention is a multi-step process involving use of various solvents, chromatography etc. and is directed specifically towards the extraction of furostanolic saponins, particularly protodioscin.

Significance of the Present Invention

As discussed above, the three major sources of FUROSTANOLIC SAPONINS are *Tribulus terrestris, Dioscorea deltoidea* and Fenugreek. Various natural preparations of FUROSTANOLIC SAPONINS based on extracts of these are available commercially, but suffer from the limitation of variation in therapeutic efficacy or desirable results. One of the major reasons for this is the large variation in the content of the active compounds or the bioactive fractions. This results in variation of results, which affects the commercial value and sale of the products. Hence, it is highly desirable to have a commercially viable process which results in high concentration of the pharmacologically active compounds in the extracts. Theoritically, it is possible to keep on enriching the fractions to obtain high concentration of bioactive compounds, but this may end up making the process commercially unviable, resulting in non-availability of commercial preparations or the availability of preparations at affordable prices, but with low content of bioactive compounds i.e. FUROSTANOLIC SAPONINS.

An illustration for the same is as follows:

*Tribulus terrestris* has been sold in the sports nutrition industry for several years apparently as a means of raising levels of the hormone, testosterone. The main components of *Tribulus* responsible for this effect are FUROSTANOLIC SAPONINS. However, as per studies available, it was found that the concentration of the pharmacologically active components i.e FUROSTANOLIC SAPONINS was much less than the desirable limits. Available research demonstrates that a person should consume between 500 mg-2000 mg of these FUROSTANOLIC SAPONINS in order to consistently get the proper response. Thus, the bioactive fractions being sold should have sufficiently high percentage of the active biological compounds i.e. FUROSTANOLIC SAPONINS. Commercially available preparations of FUROSTANOLIC SAPONINS from tribulus have been reported to be containing only 20 mg of FUROSTANOLIC SAPONINS. This practically means that a person needs at least 25-50 capsules to get the desired results in terms of efficacy. Taking such a large number of capsules, on daily basis is not practically possible.

It has been reported (Derek Cornelius, 2008 www.qfac.com/articles/syntrax/tribulus.html) that none of the commercially available *Tribulus* preparations are standardized for furostanolic saponins. At best, they are standardized for saponins. The problem is that *Tribulus* contains a fairly large proportion of spirostanolic saponins. An even further problem is that many products actually contained 40% saponins but had less than 5% furostanolic saponins. Most U.S. testing labs only test for total saponins via a simple, crude testing method. Furostanolic saponins have specific biological properties while other saponins including the spirostanolic type have not been shown to exhibit the same potent effects. Hence, it is highly desirable to have preparations with high FUROSTANOLIC SAPONINS content.

Thus, there was a need for a natural preparation which would contain the biologically active FUROSTANOLIC SAPONINS in sufficienty large concentration, so that a comfortable dose of 1-2 capsules per day could be made possible. This worked out to be 70-75% of the biologically active FUROSTANOLIC SAPONINS in the extracts.

It was found by the inventors that the natural concentration of FUROSTANOLIC SAPONINS in *Tribulus* was too less and could not result in a commercially viable process. Thus, there was a need for identification of a suitably rich source of FUROSTANOLIC SAPONINS and standardize a commercially viable process for the same. The inventor identified two potentially good sources of FUROSTANOLIC SAPONINS viz. seeds of fenugreek (*Trigonella foenumgraecum*) and rhizomes of Singly Mingly (*Dioscorea deltoidea*) from which a commercially viable process could be developed, to extract the biologically active FUROSTANOLIC SAPONINS.

Out of these two, Fenugreek was the more suitable one owing to easy availability of seeds and low cost. *Dioscorea deltoidea* suffers from the limitation that that its rhizome portion is used, which is not as abundantly available as are fenugreek seeds and is an endangered species in some countries. Moreover, Fenugreek seeds are a cheaper raw material source and starting material as compared to rhizomes of *Dioscorea deltoidea*.

A search of the Indian and International patent databases revealed that there was no process in the prior art for obtaining high-purity (>70%), bioactive, extracts of FUROSTANOLIC SAPONINS from Fenugreek seeds. Practical procedures for large scale quantitative and qualitative recovery of highly purified FUROSTANOLIC SAPONINS are lacking. The lack of suitable practical extraction and purification methods is also reflected in the relatively high cost of those extracts that are available.

Prior Art for Isolation of Furostanolic Saponins

The prior art for isolation of FUROSTANOLIC SAPONINS from plant materials broadly falls into two categories:

a) An aqueous extraction route: typically described by soaking and boiling the plant material in water resulting in the extraction of primarily water soluble compounds including saponins.

The disadvantages of the aqueous extraction method are:

Low yield: Percentage of desirable fraction obtained is quite low

Low purity: Purity of desirable fractions is very poor

Energy intensive: High temperatures are required for heating, which results in decomposition of the desired compounds.

Complicated process: Aqueous extraction of saponins i.e. 'soapy compounds' results in very high foaming which makes the overall operations complicated and difficult to control.

b) A hot organic solvent extraction process: characterized by use of polar solvents e.g. ethyl alcohol, methyl alcohol and butyl alcohol to extract compounds of interest.

The advantages of this process are:
High yield
High purity
Low energy requirements
Simple operations, as solvents are easy to evaporate which makes drying of the product fast; also there is no foaming Surprisingly, the inventors of the present invention, have determined that neither the aqueous extraction route nor the hot alcohol extraction route are particularly efficient in recovery of FUROSTANOLIC SAPONINS from fenugreek seeds, resulting in low recoveries and low purity fractions (3-5%). Thus, none of the approaches described or indicated in the prior art are practical for large scale production of high-purity (>70%), bioactive extracts of FUROSTANOLIC SAPONINS and are impractical for plants that contain mixtures of saponins.

A novel, highly efficient process from fenugreek seeds (Trigonella foenumgraecum) was developed by the inventors and same is disclosed in this application. The process results in high-purity (>70%), bioactive FUROSTANOLIC SAPONINS in which one of the bioactive fraction is protodioscin (>30%).

OBJECTS OF THE INVENTION

It is an object of the present invention to disclose a high-purity (>70%), bioactive fraction of furostanolic saponins extracted from fenugreek seeds.

One more object of the present invention to disclose a high-purity (>70%), bioactive fraction of furostanolic saponins from fenugreek seeds, in which one of the bioactive fractions is protodioscin(>30%).

Another object of the invention is to disclose a commercially viable process for the extraction of high-purity (>70%), bioactive fraction of FUROSTANOLIC SAPONINS from fenugreek seeds.

Yet another object of the invention is to disclose a commercially viable process for the extraction of high-purity (>70%) FUROSTANOLIC SAPONINS from fenugreek seeds (Trigonella foenumgraecum) which is eco-friendly as it avoids use of high temperatures or solutions of extremes of pH, the entire process being primarily carried out at or near neutral pH i.e. between 6-8 and temperature <80° C. .

Still another object is to disclose a process for the extraction of high-purity (>70%) bioactive furostanolic saponins from fenugreek seeds, which stimulate testosterone production and anabolic metabolism.

SUMMARY OF THE INVENTION

The present invention discloses a novel, commercially viable process for the extraction of high-purity (>70%) bio-active FUROSTANOLIC SAPONINS from fenugreek seeds (Trigonella foenumgraecum), primarily at low temperatures <80° C. and near neutral pH between 6 to 8. The process consists of extracting the seeds with organic solvents, concentration of the extracts, ion-exchange chromatography under specified conditions and introduction of a novel step involving use of a composite solvent for extraction of the ion-exchange column purified fractions, which surprisingly results in yield of high-purity (>70%) bioactive FUROSTANOLIC SAPONINS in which one of the active components is protodioscin (>30%).

DESCRIPTION OF THE ACCOMPANYING DRAWINGS

FIG. 1: Structure of the bioactive molecule, protodioscin
FIG. 2: Chromatogram of reference standard (chromadex) of Protodioscin
FIG. 3: Chromatogram of alcoholic extracts from Fenugreek seeds
FIG. 4: Chromatogram of the final product High-purity (>70%) bioactive furostanolic saponins from Fenugreek seeds

DETAILED DESCRIPTION OF THE INVENTION

The present invention discloses a novel, commercially viable process for the extraction of high purity (>70%), bio-active FUROSTANOLIC SAPONINS, including but not restricted to Protodioscin, from fenugreek seeds (Trigonella foenumgraecum). This is because whether single furostanol saponin or mixture of two furostanol saponins in vary ratio is responsible for testosterone stimulating effect is neither reported nor disclosed in related patents or other publications, though protodioscin is the major component of the bioactive FUROSTANOLIC SAPONINS fractions, as identified by HPLC. (FIG. 1, FIG. 2 and FIG. 3 and FIG. 4).

The process comprises the following basic steps:
extracting the appropriate plant part (fenugreek seeds) with organic solvents i.e. primary extraction
concentration of the extracts using suitable extractor such as rotary type
ion-exchange chromatography under specified conditions and
a secondary extraction step involving use of a novel composite solvent for extraction, the said novel composite solvent comprising a mixture (1:1, v/v) of chlorohydrocarbons and lower aliphatic alcohols viz. methanol, ethanol and the like
concentration and drying.

Surprisingly, the introduction of the secondary extraction step drastically enhanced the extraction efficiency, resulting in high-purity (>70%) bioactive, FUROSTANOLIC SAPONINS fractions. The high-purity (>70%) bio-active compounds i.e. furostanolic saponins with protodioscin as one of the active fractions (>30%), of the composition extracted by the process of the present invention may be derived, isolated, and/or extracted from Fenugreek seeds.

A preferred method for extracting the bio-active compounds from Fenugreek seeds, which includes the steps of:
(1) providing a plurality of Fenugreek seeds having a FUROSTANOLIC SAPONINS content of not less than 1.2%;
(2) preparing the Fenugreek seeds by milling/grinding; and
(3) extracting a novel composition of bio-active FUROSTANOLIC SAPONINS from the Fenugreek seeds, which includes a primary extraction step using organic solvents, followed by an ion-exchange chromatography step and a secondary extraction step involving use of a novel composite extraction solvent
(4) Decolorization and vacuum drying to obtain the high-purity (>70%), bio-active furostanolic saponins in powder form. Powder form facilitate easy conversion of the saponins into dosage forms such as tablets, capsules and like forms, for oral intake.

Surprisingly, the inventors found that extraction with pure alcohols is highly selective in that methanol preferentially extracts only desirable bioactive FUROSTANOLIC SAPONINS. Surprisingly, the inventors also observed that use of organic solvents and/or ion exchange purification alone was unable to enhance purity levels of the desired bioactive FUROSTANOLIC SAPONINS rich fractions to high-purity levels (>70%) as illustrated below:

The fenugreek seeds were ground and extracted with alcohol (EtOH/MeOH), followed by concentration and washing with hexane to remove oil impurities i.e. as defatting agent. This was followed by freeze drying of the extracted material, dissolving in polar solvent mixture (90:10 EtOH:water) & passed through ion-exchange (amberlite, cationic) H+ resin to remove alkaline impurities. Based on prior art concept of precipitation of saponins using acidic conditions, inventors acidified the extract using 2N sulphuric acid, followed by dispersion in Iso Propyl alcohol to crystallize out the high purity fractions. Surprisingly, this method was not at all found suitable for quantitative extraction of FUROSTANOLIC SAPONINS and resulted in very poor yield of the FUROSTANOLIC SAPONINS fractions. Also, purity levels obtained were quite low (<30%).

To overcome this problem, inventors tried using the same process but by using alumina (column chromatography) instead of ion-exchange chromatography, which is reported to be quite efficient in purification of desired compounds. Surprisingly, instead of improving the process, use of alumina not only increased time cycle, but also resulted in fractions with low purity rendering the process unsuitable for commercial applications. An attempt was made to improve purity of the obtained fractions by subjecting them to another round of chromatographic separation, but did not succeed. There was no enhancement of either quality or quantity of the desirable fractions. An innovative approach was then tried by the inventors in which permutations and combinations of various solvents were used after the ion exchange chromatography step. Surprisingly, use of specific composite solvent mixtures resulted in remarkable enhancement of purity (>70%) of the desired bioactive fractions of FUROSTANOLIC SAPONINS, including protodioscin, (>30%). It was then realized by the inventors that the unique positioning of a novel extraction step comprising of a composite solvent mixture, after the ion-exchange chromatographic step was critical in obtaining high purity (>70%) FUROSTANOLIC SAPONINS fractions. Details of the process are discussed below:

The fenugreek seeds were ground and extracted with alcohol EtOH/MeOH), concentrated by heating at temperatures of 60±5 degree celsius under vacuum followed by dispersion of the concentrated mass in water followed by ion-exchange chromatography. Surprisingly, it was observed that use of mixed bed ion-exchanger (Aromatic synthetic adsorbent, HP-20) was more efficient than simple anion exchanger but use of specific mixed bed ion-exchanger alone was not sufficient to achieve desired purity levels of FUROSTANOLIC SAPONINS.

The problem was solved by the inventors by use of a novel composite solvent after the ion-exchange step, which resulted in a remarkable improvement in the purity level of the desired FUROSTANOLIC SAPONINS saponins (>70%). It was then realized by the inventors that use of this solvent was the key to obtaining high yields of FUROSTANOLIC SAPONINS.

Surprisingly, the inventors of the present invention have found that only a narrow range of solvents can effectively extract FUROSTANOLIC SAPONINS from fenugreek seeds such as methyl alcohol, ethyl alcohol and butyl alcohol.

From the above findings, it was found that use of organic solvents and specific ion-exchange resins alone was incapable of extracting FUROSTANOLIC SAPONINS from fenugreek seeds, at desired levels of purity (>70%). Efficient separation of the FUROSTANOLIC SAPONINS could only be obtained by incorporating an additional step of secondary extraction involving use of a composite solvent, after ion-exchange chromatography. This surprisingly resulted in obtaining highly pure (>70%) FUROSTANOLIC SAPONINS at a high yield. Thus, the present invention has led to finding of a simple and easy process for producing FUROSTANOLIC SAPONINS fractions having high purity (>70%), at a commercial scale.

BEST MODE FOR CARRYING OUT OF THE INVENTION

Hereinafter, the process of the present invention is illustrated in detail.

Starting Fenugreek Seeds

The seeds used for FUROSTANOLIC SAPONINS extraction using the current method of invention are those having a FUROSTANOLIC SAPONIN content of not less than 1%. The same is determined by preparing alcoholic extracts of the seeds followed by HPLC analysis for protodioscin content (FIG. 3). Thereafter, the starting seeds are subjected to milling/grinding to enhance surface area and thus efficiency of extraction process.

Extraction Solvent

Following the milling/grinding operations, the seeds are subjected to organic solvent extraction. Particularly suitable solvents for the process of the invention are hydrophilic polar solvents including lower aliphatic alcohols such as methanol, ethanol and butanol. It is not advisable to use non-polar organic solvents such as ether, chloroform etc. because they have inferior extraction efficiencies with respect to FUROSTANOLIC SAPONINS.

Extractor

It is pertinent to mention here that the extraction vessel used is specifically of the rotary type design to ensure efficient extraction and use of less quantity of solvents. In addition, it also helps minimize solvent losses.

Extraction Temperature

Extraction of FUROSTANOLIC SAPONINS from fenugreek seeds is preferably carried out at temperatures below 80 degree Celsius, to avoid loss of structural integrity and bioactivity of the desired FUROSTANOLIC SAPONINS. High temperatures are detrimental to protodioscin activity. Hence, entire extraction process was carried out below 80 degree Celsius, preferably between 40-65 degree Celsius which was found to be optimal for the process. In case, extraction is carried out at temperatures lower than the specified range, extraction efficiency is found to be reduced and leads to lower yields, thus affecting commercial viability.

Extraction pH

The process specifically avoids use of extremes of pH and is carried out at or near neutral pH, preferably 6-8. Too high a pH results in poor separation efficiency of FUROSTANOLIC SAPONINS from fenugreek seeds, while too low a pH results in undesirable precipitates. The optimum neutral pH for the process thus offers the advantage of safe working, easy handling of the solvents and safety of equipments.

Extraction Method

Appropriately selected fenugreek seeds, duly milled/ground are subjected to primary extraction. The extraction is carried out by use of organic solvents, at a weight volume ratio of which can range between 1:3 to 1:5 for each extraction. In present process, an optimum seed:solvent ratio of 1:4.5 per extraction was used. The preferred solvents are lower aliphatic alcohols such as methanol, ethanol and butanol. Optimally, three extractions are carried out, followed by concentration by heating, at a temperature between 55-65 degree Celsius.

Purification Method

The concentrated fraction is diluted with a highly polar solvent such as water, in an optimal ratio of 1:10 and is subjected to ion-exchange chromatography using HP-20/PA-500 mixed bed resin. The purified fraction rich in FUROSTANOLIC SAPONINS, so obtained is concentrated by heating and eventually dried completely under vacuum. The dried mass is then extracted twice using a novel composite solvent comprising chlorohydrocarbon:alcohol (1:1, v/v) to obtain the desired, high-purity (>70%), bioactive, furostanolic saponin fractions including protodioscin (>30%). Preferably, the chlorohydrocarbon used is methylene dichloride and alcohol is methanol. This composite solvent was found to be surprisingly efficient in extracting the FUROSTANOLIC SAPONINS of interest.

Treatment of Extract with Adsorbent and Concentration

The FUROSTANOLIC SAPONINS rich solvent as obtained above is then decolorized using activated charcoal followed by filtration to remove the same. The decolorized fraction is concentrated by heating at a temperature of 40-50 degree Celsius, under vacuum not less than 650 mm Hg.

Processing of the Furostanolic Saponins Rich Fraction and Obtaining Final Product The concentrated mass obtained is dried under vacuum using vacuum tray drier or spray drier or any other suitable conventional technique. The lumps obtained are ground and sieved using an in vibro-sifter to a mesh size of about 40-60 mesh. Packaging is done in bulk powder form only, which is the final high-purity (>70%), bioactive, furostanolic saponin fractions including protodioscin (>30%).

Method for Determination of Furostanolic Saponins

The same was carried out using HPLC. Table 1 below shows the conditions of HPLC analysis.

TABLE 1

| Parameters | HPLC conditions |
| --- | --- |
| COLUMN | Nucleosil 5u ODS |
|  | 250 × 4.6 mm |
| FLOW RATE | 1.0 ml/min |
| INJECTION VOLUME | 20 μl |
| DETECTOR | UV, with PDA 205 nm |
| RUN TIME | 35 min |
| COLUMN OVEN TEMPERATURE | 30° C. |
| MOBILE PHASE | HPLC WATER:ACN (1:1) |
| STANDARD/SAMPLE PREPARATION (FUROSTANOLIC SAPONINS rich fraction) | 1000 ppm In Methanol |
| HERB (Fenugreek seeds) | Extract 1.0 gm powdered seed in 100 ml MeOH Filter and inject directly.(1:100) |

The active fractions of FUROSTANOLIC SAPONINS with Protodioscin as one of the major biologically active component is analysed by HPLC, using Protodioscin as the reference standard and as per conditions given in Table 1. Chromatograms of the reference and the fractions obtained from fenugreek seeds are given in FIG. 2, FIG. 3. and FIG. 4.

The invention is further illustrated by the following example below which describes the preparation of a high-purity (>70%), bioactive FUROSTANOLIC SAPONINS fractions including protodioscin (>30%), on commercial scale from fenugreek seeds. The example is not intended to limit the effective scope of the claims but is intended for illustrative purposes to enable better understanding of the process.

EXAMPLE 400 kg seeds of *Trigonella foenumgraecum* are powdered and loaded in Rotary type extractor followed by 1800 liters of alcohol (1:4.5), stirred for 3-4 hrs at 40±5° C. then filtered and the extraction carried with 1600 liters of alcohol, thrice. Exhaustion of the herb is monitored by TLC using Vandroff reagent.

The extracts are combined and concentrated. The residue obtained is 15-20% of the input. The residue is further diluted with water (1:10) and checked for pH. If required suitable neutralization is carried out by addition of ammonia or sodium bi-carbonate. The extracts are filtered and the filtrate is passed through Ion Exchange mixed bed resin (Pure size 400 angstrom and surface area 500 $m^2/gm$) at a flow rate of 50 lit-100 lit/hr. Then solvent comprising 1:80 water is passed through the column to remove the celluloses and oil particles. This is followed by increased % of alcohol to 10% (1:20) so as to remove the slightly polar compound and maintaining flow rate of 100 lit/hr. The material is eluted with 100% alcohol (i.e. 1:10) and concentrated under controlled condition (temp. <65° C. and vacuum NLT 650 mm Hg). Concentrated mass is dried in vacuum tray drier. Product obtained is 13.5 kgs of marked compound 25% and FUROSTANOLIC SAPONINS 55%. The above material is further dispersed in approximately 100 liters (1:7) composite solvent (methanol: methylene dichloride: 1:1). Mixture is filtered and the solid material is dispersed again 1-3 times, optimally one more time in the same ratio as of $1^{st}$ extraction. Filtrate is combined, decolorized, filtered, and concentrated under controlled conditions (temp. <50° C. & vacuum not less than 650 mm Hg. Concentrated mass is further dried in a vacuum tray drier. Product obtained is approximately 10 kgs of product (FUROSTANOLIC SAPONINS>70% including protodioscin >30%). This product meets the required specifications of quality and quantity.

INDUSTRIAL APPLICABILITY

The process for extraction of FUROSTANOLIC SAPONINS as disclosed in the present invention is suitable for industrial-scale preparation of high-purity (>70%) bioactive, FUROSTANOLIC SAPONINS including protodioscin (>30%). The fractions obtained may be used for pharmaceutical/nutraceutical applications. The high-purity (>70%), bioactive fractions in powder form facilitate easy formulation of the same into convenient oral dosage forms such as capsules, tablets and the like.

Although the invention has been described with reference to specific embodiments, this description is not meant to be construed in a limiting sense. Various modifications of the disclosed embodiments, as well as alternate embodiments of the invention, will become apparent to persons skilled in the art upon reference to the description of the invention and best mode of performing the invention. It is therefore contemplated that such modifications can be made without departing from the spirit or scope of the present invention as defined.

I claim:

1. An extract obtained from fenugreek seeds by a commercially viable process comprising the steps of:
   providing plurality of fenugreek seeds and crushing the same by milling and grinding;
   performing a primary extraction on the prepared fenugreek seeds using a first hydrophilic polar solvent which is a lower primary aliphatic alcohol followed by ion-exchange chromatography;
   performing a secondary extraction after ion-exchange chromatography using a composite solvent which is a mixture of a chlorohydrocarbon and an aliphatic alcohol; and
   decolorizing the final extract by use of activated charcoal concentration of the extract by heating and vacuum drying sieving the final powdered product, wherein
   seeds used in the extraction process have a furostanolic saponin content of not less than 1%,
   the extraction process is carried out below 80 degree Celsius, and wherein the final extract comprises a mixture of five furostanolic saponins in which protodioscin is one of the marker compounds, as measured by HPLC.

Figure 4:
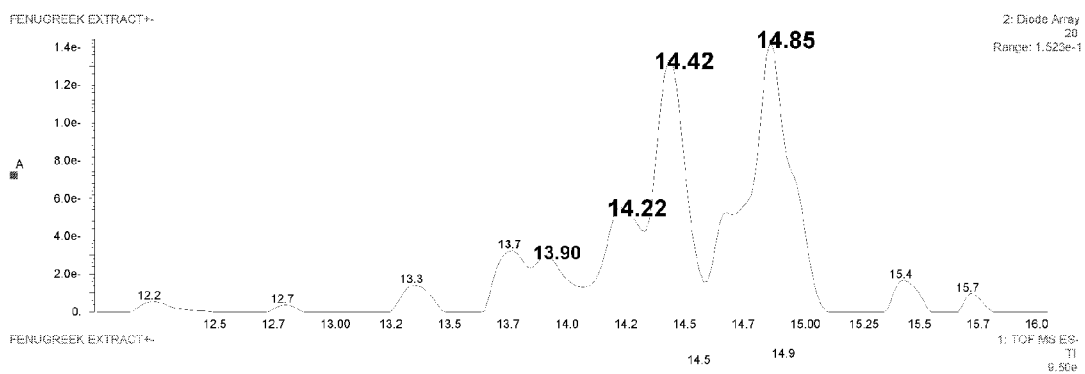

2. The extract obtained from fenugreek seeds by a commercially viable process comprising the steps of:
   providing plurality of fenugreek seeds and crushing the same by milling and grinding;
   performing a primary extraction on the prepared fenugreek seeds using a first hydrophilic polar solvent which is a lower primary aliphatic alcohol followed by ion-exchange chromatography;
   performing a secondary extraction after ion-exchange chromatography using a composite solvent which is a mixture of a chlorohydrocarbon and an aliphatic alcohol; and
   decolorizing the final extract by use of activated charcoal concentration of the extract by heating and vacuum drying sieving the final powdered product, wherein
   seeds used in the extraction process have a furostanolic saponin content of not less than 1%,
   the extraction process is carried out below 80 degree Celsius, and wherein the final extract comprises a mixture of five furostanolic saponins in which protodioscin is one of the marker compounds, as measured by HPLC,
   wherein the final extract comprises a mixture of five furostanolic saponins in which protodioscin is one of the marker compounds, as shown in FIG. 4.

* * * * *